United States Patent [19]

DeSatnick

[11] Patent Number: 4,674,500
[45] Date of Patent: Jun. 23, 1987

[54] SHEATHED KNIFE INSTRUMENT

[75] Inventor: Allen H. DeSatnick, Marblehead, Mass.

[73] Assignee: Minnesota Mining and Manufacturing Company, St. Paul, Minn.

[21] Appl. No.: 780,895

[22] Filed: Sep. 27, 1985

[51] Int. Cl.$^4$ .............................................. A61F 17/32
[52] U.S. Cl. ...................................... 128/305; 604/22; 30/286
[58] Field of Search ............... 128/305, 317, 318, 314, 128/304; 604/22; 30/280, 282, 286, 289, 291, 294

[56] References Cited

U.S. PATENT DOCUMENTS

| 1,339,692 | 5/1920 | Diamant . | |
|---|---|---|---|
| 2,131,780 | 10/1938 | Storz | 128/309 |
| 2,258,287 | 10/1941 | Grieshaber | 128/309 |
| 2,843,128 | 7/1958 | Storz | 128/309 |
| 3,835,859 | 9/1974 | Roberts et al. | 128/305 |
| 4,067,340 | 1/1978 | Le Noir | 128/305 |
| 4,491,132 | 1/1985 | Aikins | 128/305 |

FOREIGN PATENT DOCUMENTS 853410 3/1940 France .
114998 6/1925 Switzerland .................. 128/305

Primary Examiner—Henry A. Bennet
Attorney, Agent, or Firm—Donald M. Sell; James A. Smith; Robert W. Hoke, II

[57] ABSTRACT

A surgical instrument comprising an elongate reusable handle and disposable, interchangeable sheathed blade modules. Each sheathed blade module including an elongate tubular sheath having a laterally arced blade guiding forward end portion of either a cylindrical or tubular configuration. The arced portion defines a guide path for a blade received within the sheath. The blade, through interconnection with a slide member on the handle module, is selectively moved between a first protected position entirely within the sheath and a second position wherein the surgical tip portion of the blade is exposed. Outward movement of the blade tip portion is directed along a predetermined path by the curved forward end portion of the sheath, while at the same time providing for a complete exposure of the blade tip portion beyond the structure of the sheath. The slide member of the sheath is controlled by a single finger of the one hand used to hold the handle module.

22 Claims, 12 Drawing Figures

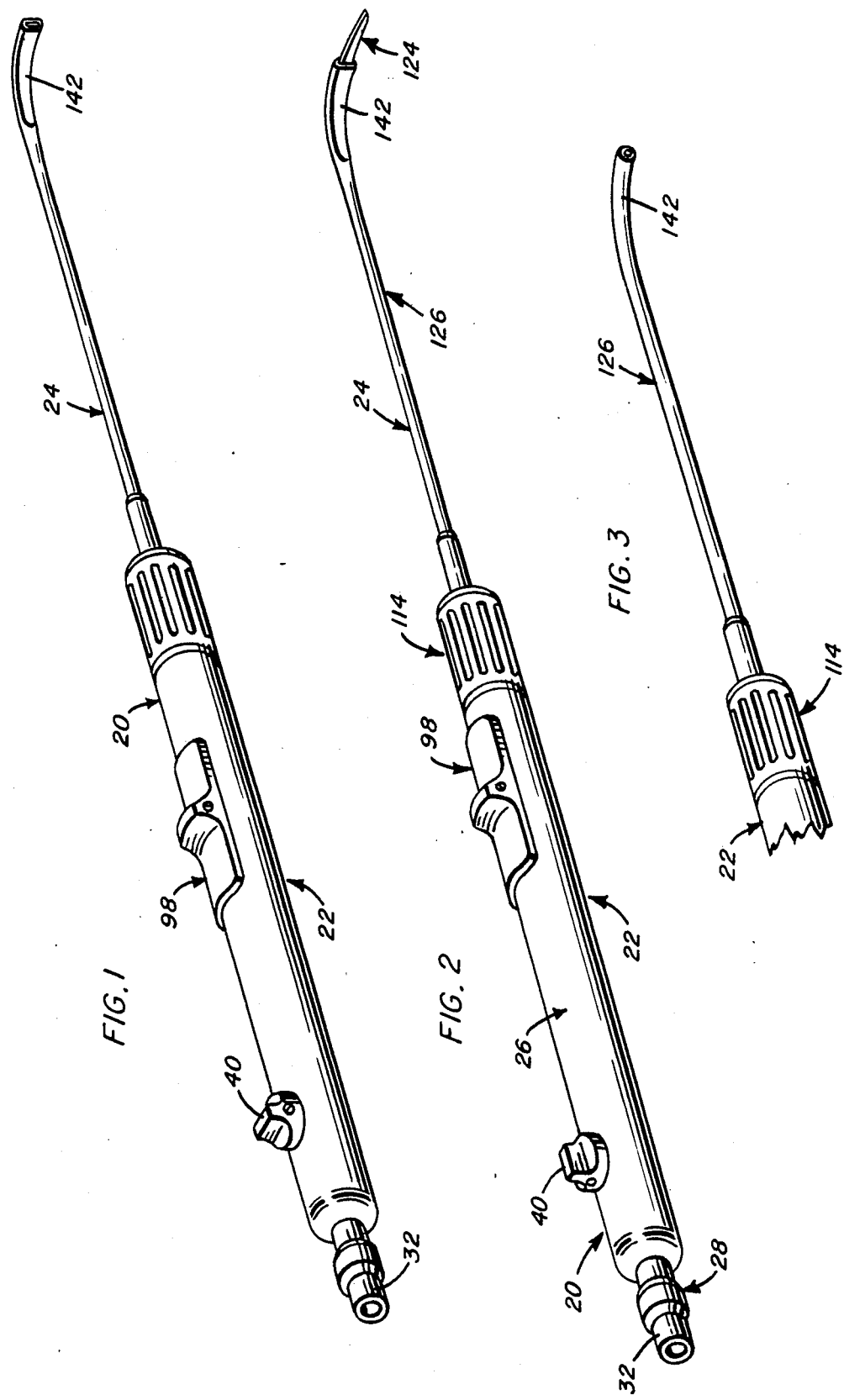

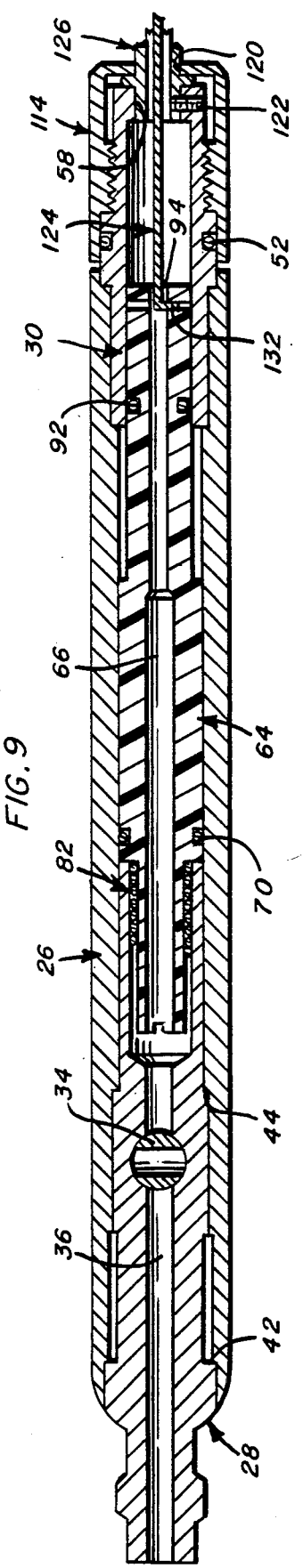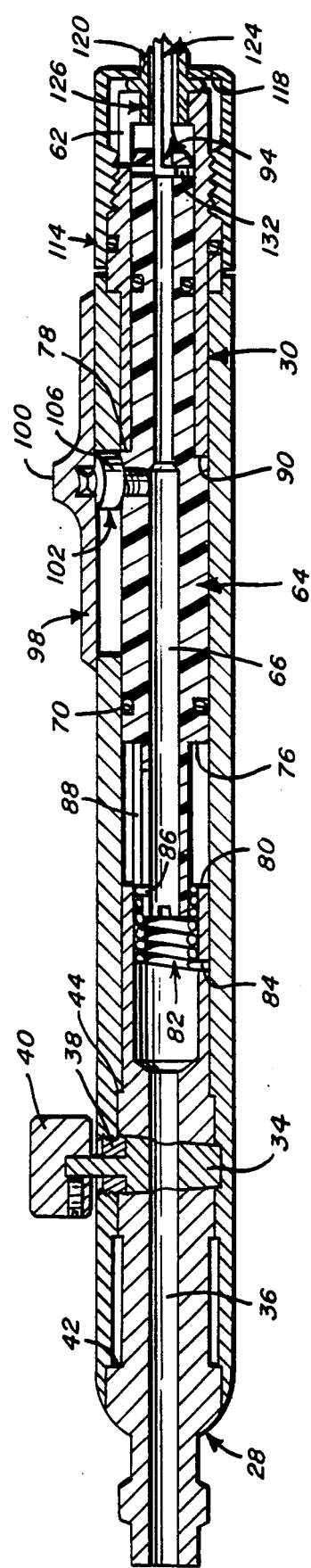

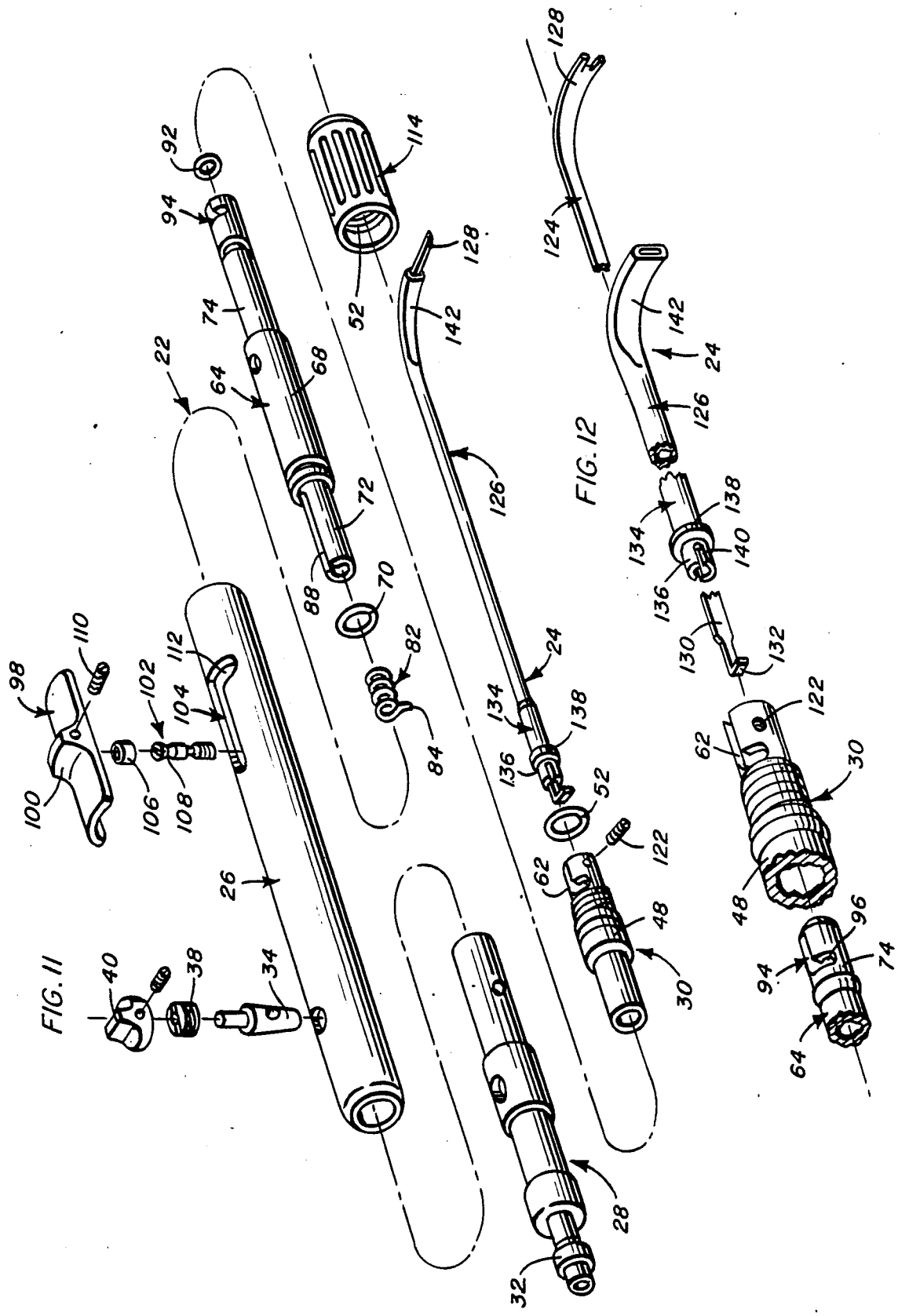

SHEATHED KNIFE INSTRUMENT

BACKGROUND OF THE INVENTION

The present invention is broadly directed to surgical instruments, and more specifically to instruments useful in arthroscopic surgery and similar surgical procedures wherein access to the surgical site is limited and/or difficult.

The surgical environment of the invention normally involves performance of surgical procedures through small incisions through which the instruments are introduced and subsequently manipulated. With the use of surgical cutting instruments, for example cutting blades, substantial care must be taken not only in the cutting manipulation thereof, but also in the actual introduction of the cutting blade to the cutting site and the subsequent removal therefrom.

As noted in substantial detail in Aikins, U.S. Pat. No. 4,491,132, issued Jan. 1, 1985, one known procedure for the atraumatic introduction of a cutting instrument utilizes a protective sheath. The sheath, a linear hollow member, has the blade completely received and sheathed therein. The blade remains in the sheath until the distal or forward end of the sheath is positioned proximate the site of use. At that time, the blade is mechanically extended from the sheath, either by an actual extension of the blade from the sheath or by a corresponding retraction of the sheath relative to the blade. The Aikins patent notes the desirability for such instruments and discloses selected variations thereof.

The necessity for surgical procedures in limited access environments has also led to the development of instruments incorporating means for guiding a cutting blade or the like during the actual use thereof at the cutting site. Such known means include opposed guides or tracks along which the blade travels during the cutting operation. In this regard, note the following:
Roberts et al; U.S. Pat. No. 3,835,859; Sept. 1, 1974
Le Noir; U.S. Pat. No. 4,067,340; Jan. 10, 1978

The instrument in Roberts et al is limited in its use in that the guided nature of the blade enables use of the blade only for a removal or slicing of material from a surface. It cannot be used to make a perpendicular cut. Further, the instrument itself is rather cumbersome, requiring the use of two handles to adjust the wire shape and position, after which the blade has to be moved forward in a separate motion.

The Le Noir instrument has been devised for a specific procedure, and is not readily adaptable for general cutting purposes in either arthroscopic surgery or other surgery. Further, the tool itself is rather cumbersome and utilizes two insertions to position and align the opposed guide grooves to carry the flexible blade therebetween.

SUMMARY OF THE INVENTION

The surgical instrument of the present invention is unique in its provision of a sheath protected blade wherein the sheath, in addition to performing its protective function, is configured, along the distal end portion, to both guide and direct a received blade along a preselected laterally curving path.

In conjunction with the specific configuring of the sheath itself as a means for providing for a guiding of the blade, it is also significant that the guided leading tip and end portion of the blade be extended and operable beyond the confines of the guide structure of the sheath while maintaining the preselected guided path defined by the distal end portion of the sheath. In this manner, the operative end of the blade is completely exposed for free use of its tip and/or edge as required by the particular procedure. The complete exposure of the operating end portion of the blade, while providing for a positive guidance thereof along for example an arcuate path, provides for not only an exact positioning of the blade, but also, as desired, a guided cutting motion as the blade is slid out of the sheath and along the guided path.

The sheathed knife instrument of the invention provides a reusable handle and actuation mechanism in conjunction with removable, disposable single use sheathed knife blades. The sheathed blades are easily interchangeable and can be provided with a variety of different blade guiding curvatures at the distal ends of the sheaths. Similarly, variations in blade widths and tip shapes can be easily provided by provision of appropriately configured sheath and blade combination assemblies interchangeably mountable on the handle.

It is also considered a significant object of the invention to provide a surgical instrument which can be particularly adapted for use as a multi-function probe, knife, and aspirator/irrigator.

The construction of the surgical instrument involves two basic modules, the reusable handle and the disposable combination sheath and blade.

The reusable handle is a small, round elongate cylindrical tube easily grasped and manipulated by one hand. An elongate cylindrical tubular slider is mounted for reciprocation within the main cylindrical body of the tube. The internal slider is connected to an external slide button whereby the handle can be held in one hand and the external button actuated either by the thumb or an index finger for a selective reciprocation of the internal slider. In those instances wherein the instrument is to accommodate fluid flow, either as an aspirator or irrigator, a valve and tube fitting will be incorporated in the rear section of the handle. The desired flow will be effected through the tubular handle and tubular internal slider. Appropriate seals will of course be provided. The handle assembly or module also includes a retaining cap mounted on the front or forward section thereof and used to removably retain the disposable sheathed blade.

The disposable sheathed blade is a two-part assembly comprising the blade and the surrounding sheath. The rear or proximal portion of the sheath is configured for positioning within the front or forward section of the handle for retention by the retaining cap. The forward or distal portion of the sheath will preferably be of either a flattened or a tubular configuration, in each instance following a lateral arcuate curvature corresponding to the guided direction desired for the blade. The flattened end configuration allows for access to smaller areas along with higher fluid velocities. The tubular or unflattened cylindrical end portion provides for higher fluid flows. Either configuration can be given any curvature.

The elongate flexible blade is slidably received within the sheath and, when extended, follows the sheath curvature. The flexible nature of the blade enables the blade to assume the curvature of the sheath and retain this curvature as the leading end portion of the blade is extended from the sheath. As desired, the blade may be formed with a predisposition to assume the particular curvature of the sheath with which it is associated.

The blade, at the rear or proximal end thereof, includes a laterally directed tab which is removably positioned within the leading end of the slider for a manipulation of the blade in response to sliding movement of the slider. The rear or proximal end of the sheath is, in turn, retained to the leading end of the handle by the retaining cap with the blade movable relative thereto. Replacement of the blade and sheath combination requires only a removal of the retaining cap and a disengagement of the blade. A new assembly is then inserted into place and the retaining cap remounted. The leading portion of the blade or blade tip can be provided with any appropriate surgical configuration. Similarly, the blade and sheath assemblies can be made to any necessary blade width and any desired operating curvature.

BRIEF DESCRIPTION OF THE DRAWINGS

FIG. 1 is a perspective view of the sheathed knife instrument of the present invention with the blade retracted;

FIG. 2 is a perspective view similar to FIG. 1 with the blade extended;

FIG. 3 is a partial perspective view of the forward portion of the instrument wherein the sheath is provided with a cylindrical forward guide portion;

FIG. 9 is a longitudinal cross-sectional view through the instrument rotated 90 degrees from the showing in FIG. 4 with the blade in its retracted position;

FIG. 10 is a longitudinal cross-sectional view rotated relative to FIG. 9 with the blade in the extended position with the valve open and the slide button locked, the button connector, for purposes of clarity, is shown in elevation;

FIG. 11 is an exploded perspective view of the components of the instrument; and FIG. 12 is an exploded perspective detail of the sheath and blade module and the mounting portions of the handle module.

DESCRIPTION OF THE PREFERRED EMBODIMENT

Figure 4:
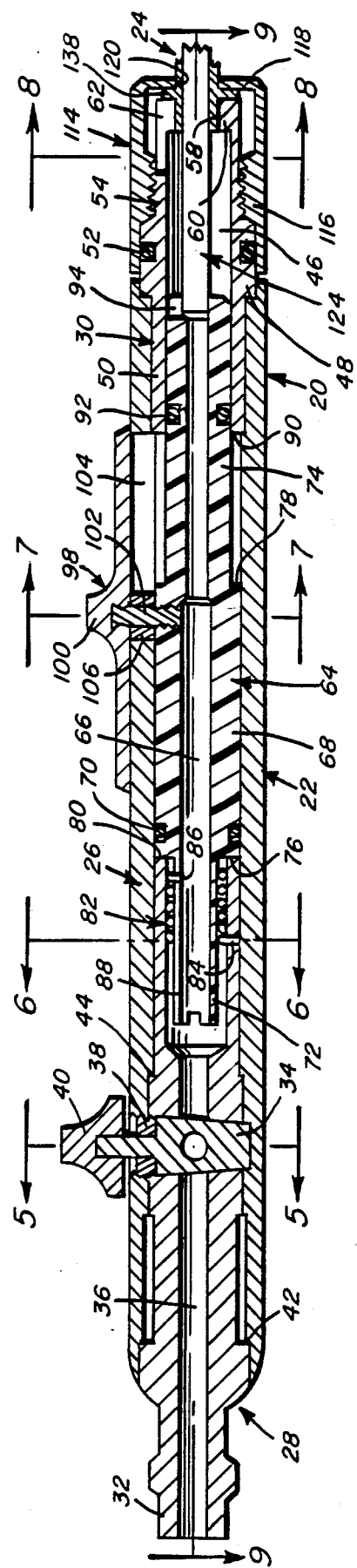
FIG. 4 is an enlarged longitudinal cross-section through the instrument with forward portions of the sheath and blade broken away.
Figure 8:
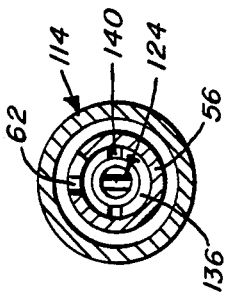
FIG. 8 is a cross-sectional detail taken substantially on a plane passing along line 8—8 in FIG. 4.
Figure 7:
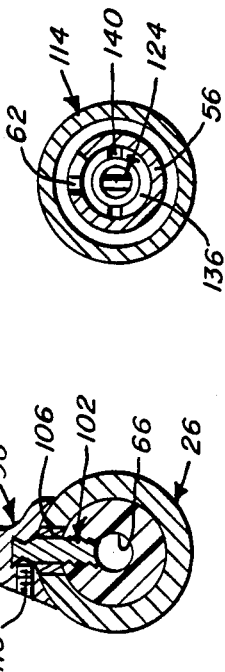
FIG. 7 is a cross-sectional detail taken substantially on a plane passing along line 7—7 in FIG. 4.
Figure 6:
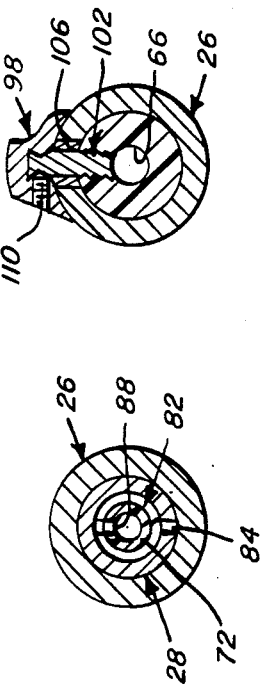
FIG. 6 is a cross-sectional detail taken substantially on a plane passing along line 6—6 in FIG. 4.
Figure 5:
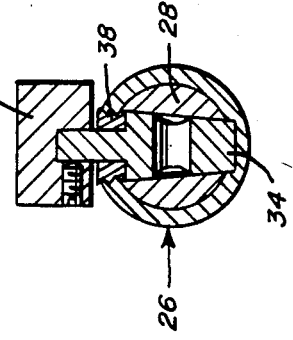
FIG. 5 is a cross-sectional detail taken substantially on a plane passing along line 5—5 in FIG. 4.

Referring now more specifically to the drawings, reference numeral 20 is used to generally designate the surgical instrument comprising the present invention. The instrument, principally a sheathed blade knife, comprises two basic modules, a reusable handle 22 and a disposable sheathed blade or combination sheath and blade 24. The sheathed blade 24, as shall be detailed subsequently, is operably mountable to the handle for manipulation thereby. After use, the sheathed blade is removed and disposed of, while the handle is retained for reuse.

The handle 22 comprises an elongate main cylindrical tubular body 26 having rear and forward tubular sections 28 and 30 longitudinally aligned with and telescopically press fit within the rear and forward portions respectively of the main body 26. The press fit engagement is such as to provide a fluid tight seal, this being particularly significant in those instances wherein the instrument is also to perform an aspirator/irrigator function. In such cases, and as illustrated in the drawings, the rear section 28 will be provided with a coaxial rearwardly directed nipple 32 for engagement, through appropriate tubing, with a fluid source, vacuum chamber, or the like.

In cases of fluid flow, control thereof directly from the handle is desired. As such, an appropriate valve, such as plug valve 34, can be mounted transversely of the flow passage 36 through the rear portion 28. The valve, as illustrated, is rotatably retained by a threaded retaining ring 38 engaged about the stem of the valve and threaded within an internally threaded bore in the main body 26 through which the valve 34 is introduced. The valve stem projects externally of the body and mounts an appropriate valve manipulating knob 40, configured for easy grasping between the fingers of a user for rotation of the valve, in either direction, between an open and closed position. With continued reference to the knob 40, it will be noted that the gripping configuration thereof actually defines an elongate projecting rib which can be oriented on the stem of the valve to visually indicate the open and closed positions thereof.

The proper positioning of the rear section 28 within the main body 26 is provided for by interengaging or seating annular shoulder portions exteriorly about the rear section 28 and interiorly about the hollow bore of the body 26 as illustrated at 42 and 44.

The forward or front section 30 is also of a tubular open ended configuration, the hollow interior of which, designated at 46, may define a fluid passage.

An integral annular collar 48 surrounds the front section 30 at approximately midpoint along the length thereof. The proximal portion 50, rearward of the collar 48, is press fit within the forward end portion of the main body 26 with the rear portion of the collar 48 seated within an annular seat at the forward end of the body 26. The engagement of the forward section within the forward portion of the body, as previously noted, preferably provides a fluid tight seal.

The collar 48, forward of the front end of the main body 26, is provided with an annular O-ring seal 52 appropriately seated within an annular retaining groove. Immediately forward of the collar 48, the front section 30 includes an exteriorly threaded portion 54. The front section 30, forward of the threaded portion 54, includes a smooth tubular integral extension 56 terminating in an end wall with a central aperture 58 of slightly less diameter than the internal bore 46 resulting from an integral collar-like internal enlargement 60 at the forward end of front section 30.

In order to receive and properly orient the sheathed blade module 24, as shall be detailed subsequently, the tubular forward portion 56 of the front section 30 includes a slot 62 extending longitudinally therein from the outer forward end and terminating in a transverse or laterally directed inner end portion immediately forward of the externally threaded portion 54, providing in effect an L-shaped slot communicating with the longitudinal interior bore 46 of the forward section 30 throughout the length of the slot. As will be appreciated from FIG. 4 in particular, the slot extends through the internal thickening or collar 60 defining the forward aperture 58.

The handle 22 includes an elongate internal tubular slider 64 preferably having a hollow open-ended full length axial bore 66 adapted to accommodate fluid flow in those instances wherein the instrument is structured to provide for such flow. This axial bore 66 will provide continuity between the passages or bores 36 and 46 of the rear and forward sections 28 and 30.

The internal slider 64 includes an elongate central portion 68 closely received within and slidable along the internal bore of the main body section 26. This central slider portion 68 is suitably sealed to the bore wall by an appropriate O-ring seal seated within a retaining groove about the outer periphery of the central portion 68.

The internal slider 64 includes elongate reduced diameter integral and coaxial rear and forward portions 72 and 74. Each of these portions 72 and 74 define, at the corresponding end of the central portion 68, an annular external shoulder 76 and 78 respectively.

The rear portion 72 of the internal slider 64 is telescopically received within the forward portion of the fluid passage or bore 36 through the rear section 28 and is adapted for free longitudinal movement therein with rearward movement of the slider limited only by engagement of the annular shoulder 76 against the forward end 80 of the rear section 28. Such an engagement will be noted in FIGS. 4 and 9, and constitutes the innermost position of the internal slider 64.

The rear portion 72 of the internal slider 64, within the forward section of the bore 36, is surrounded by a coiled torsion spring 82 having a rear laterally directed end 84 engaged within a socket in the internal wall of the bore 36 for a positioning and retention of the spring 82. The second end 86 of the spring 82 is laterally inwardly directed and received within an elongate slot or groove 88 in the rear portion 72 in a manner whereby the internal slider, while freely longitudinally slidable relative to the spring 82, is rotatably biased, when viewed from the rear thereof, in a clockwise direction relative to the central portion 26 of the handle. The significance of this feature will be explained subsequently.

The forward portion 74 of the internal slider 64 is telescopically receivable within the internal bore 46 of the front section 30 with forward sliding movement of the internal slider 64 being limited by engagement of the forward annular shoulder 78 against the annular inner or rear end 90 of the front section 30. This engagement will be noted in FIG. 10. An appropriate sealing O-ring 92 is provided, within an annular recess about the forward portion 74, between the forward portion 74 and the internal wall of the bore 46 of the front section 30. This sealed relationship is maintained throughout the full longitudinal movement of the internal slider 64.

The leading end of the forward portion 74 of the internal slider 64 has a slot 94 defined therein. This slot 94, which may communicate with the hollow interior or the interior bore 66 through the internal slider 64, extends longitudinally inward from the extreme end of the forward portion 74 and terminates, inward or rearward of the forward end, in a laterally directed extent or length 96, best noted in FIGS. 10 and 12. As desired, the laterally directed extent 96 of the slot 94 may extend to either or both sides of the main or longitudinal extent of the slot 94.

The slot 94, upon a forward extension of the slider 64 to its extended position wherein annular shoulder 78 engages against abutment end 90 of the front section 3, aligns with the slot 62, in front section 30, laterally inward thereof. This alignment will be noted in FIG. 10.

Movement of the internal slider 64 is achieved by a single thumb or finger manipulation of an external slider or slide button 98 overlying and conforming to the external configuration of the main handle body 26. To ensure a proper finger engagement with the button 98, an appropriate integral transverse rib 100 is preferably defined thereon.

The external button 98 is rigidly coupled to the internal slider 64 by an elongate connector or connector pin 102 having the inner end portion thereof provided with external threads and threadedly engaged within an internally threaded socket within the wall of the internal slider, normally immediately rearward of the annular shoulder 78. The connector 102, immediately outward of the internal slider, extends transversely through a longitudinally elongate slot 104 through the main body 26 of the handle 22. The connector 102, within the slot 104, is surrounded by a bushing 106 which facilitates free sliding movement of the connector 102 along the slot 104. The upper or outer end of the connector 102 includes an annular groove or undercut portion 108 for the reception of the inner end of an appropriate locking or set screw 110 engaged through the slide button 98 for a locking of the button 98 to the connector 102. When assembled, the internal slider 64 and the external manipulating button 98 are movable as a unit through manipulation of the button 98.

Noting FIG. 11 in particular, the forward end of the connector-accommodating slot 104 includes a laterally directed extent or length 112 whereby, upon a full forward extension of the button 98 and internal slider therewith, a lateral or rotational movement of the button 98 will result in a movement of the bushing-surrounded connector 102 into the lateral extent 112 and a locking of the internal slider in its forwardmost position. Such an arrangement is basically illustrated in FIG. 10 with the connector and bushing shown in elevation for purposes of clarity.

The previously described torsion spring 82 specifically functions to rotatably bias the internal slider 64 for movement of the connector 102 into the lateral extent 112 of the slot 104 and thus effect an automatic locking of the internal slider 64 in its forward or extended position. It is to be appreciated that this biasing force can be easily overridden by finger pressure on the slider button 98 as desired, both during actual manipulation of the instrument or at such time as a retraction of the blade is desired.

The final component of the handle module 22 is the retaining cap 114 received over and enclosing the forward projecting end portion of the front section 30. The cap includes an intermediate internal portion 116 internally threaded for threaded engagement with the externally threaded portion 54. Immediately rearward of the internally threaded portion 116, the retaining cap 114 is provided with a skirt which engages over and about the O-ring seal 52 for an internal sealing of the cap.

The forward or outer end 118 of the cap 114 has a central aperture 120 defined therethrough for an accommodation of the sheathed blade module 24.

With reference to FIG. 9, a positioning pin 122 is engaged through the enlarged leading end of the front section 30 and projects radially into the end opening 58 for cooperation with the slider slot 94 in properly orienting the sheathed blade module 24.

The sheathed blade module 24 is a two-part assembly comprising an elongate blade 124 and a tubular sheath 126.

The blade 124, at the distal or leading end portion 128 thereof, will be of any appropriate surgical configuration, for example, a knife edge as suggested in FIGS. 2 and 11, or a transverse cutting tip as suggested in FIG. 12.

The proximal or rear end portion 130 of the blade 124 includes a gripping tab 132 defined by a lateral turning or directing of the proximal end. This end portion 130 is particularly configured for introduction through the angled slot 62 in the front section of the handle for subsequent seated reception within the aligned angled slot or notch 94 of the forward portion 74 of the slider 64. As previously suggested, the positioning of the proximal end portion 130 of the blade 124 into the slider slot 94 requires a positioning of the internal slider at its forwardmost location and prior to the rotational locking thereof into the extension 112 of the slot 104 in the main body section 26.

The tubular sheath 126 will normally be of a cylindrical configuration provided with a proximal end portion 134 including a mounting end 136 and an integral seating or positioning collar 138 immediately forward thereof. The mounting end 136, constituting an integral rearward extension of the sheath, will include one or more positioning slots 140 extending longitudinally therein and opening through the rear of the sheath 126.

The forward or distal end portion 142 of the sheath 126 is laterally arced along a predetermined curvature defining the path to be taken by the blade during extension thereof. This arcuate leading portion 142 of the sheath 126 can, as illustrated in FIGS. 1 and 2, be flattened or, as illustrated in FIG. 3, be retained cylindrical throughout the extent thereof. In each instance, the particular cross-sectional configuration of the leading portion 142 of the sheath 126 will be determined by the circumstances and procedures involved. Each configuration incorporates particular advantages and will be chosen accordingly. For example, the flattened, oblong configuration, more clearly illustrated in FIGS. 11 and 12, provides maximum resistance to blade rotation, allows for access to smaller areas, and, in those instances wherein there is to be a fluid flow through the instrument, provides for higher fluid velocities. The tubular or unflattened cylindrical end portion, as illustrated in FIG. 3, will enable higher fluid flows.

The sheathed blade assembly 24 is a disposable unit with the blade 124 normally initially introduced into the sheath 126 through the rear of the sheath 126. The blade 124 is receiprocal within the sheath for a selective complete retraction of the leading forward operational portion of the blade and a corresponding extension thereof. The curved leading portion 142 of the sheath 126 is configured, in accord with the particular procedure, to both particularly position the extended blade and to guide the blade during the extension thereof beyond the sheath. The guidance of the blade during the extension thereof insures movement of the blade along a predetermined path beyond the sheath while at the same time freely exposing the blade for cutting, trimming, etc. in a controlled manner by a finger operated manipulation of the blade and a hand manipulation of the handle.

The sheathed blade assembly is, in its entirety, intended to be a disposable item, readily interchangeable as desired. It is contemplated that sheathed blade assemblies, in different widths, curvatures and blade tip configurations be provided, enabling, through the interchangeable nature of the sheathed blades, a ready adaptation of the instrument as required to any particular procedure involved. As suggested in the drawings, the rear or proximal mounting end portions of the sheaths and blades will be standardized for all sheath and blade sizes to enable accommodation within single size reusable handles. Note the mounting end portion of the illustrated sheath is of a slightly greater cross-section than the cross-section of the remainder of the sheath. Similarly, the mounting end portion of the illustrated blade is of a slightly less height.

In conjunction with the above, it is contemplated that the blades be of a flexible surgical metal capable of following the curvature of the leading portion 142 of the sheath and maintaining the directional orientation as the leading tip portion of the blade moves outward into operational position beyond the sheath. The flexible nature of the blade 124 allows for a complete retraction of the blade into the sheath for a complete protective enclosing of the blade, protecting both the blade and the body tissue during both the insertion and removal of the instrument.

In mounting the removable sheathed blade assembly 24 on the handle 22, the internal slider 64 is moved to its forward position, orienting the slot or notch 94 in the leading end beneath and in alignment with the slot 62 in the leading end of the front section 50. The rear portion 130 of the blade 124, extended rearward of the sheath 126, is then moved through the slot 62 and into retained position within slot 94. When so located, the lateral tab 132 of the rear portion 130 of the blade 124 seats within the lateral extent 96 of slot 94. The width of the tabbed rear portion of the blade is such as to move completely through the slot 62 and seat within the slot 94 of the leading end of the internal slider 64. When so positioned, the engagement with the slider is such whereby the blade 124 will both longitudinally reciprocate and rotate with the internal slider in response to movement of the internal slider. The notched seat defined by the slot 94 precludes all relative movement between the blade 124 and the internal slider 64 other than for a complete disengagement of the blade and a removal thereof upon an alignment of the outer slot 62 therewith.

After a seating of the inner portion of the blade within the notch defined by slot 94, the mounting end 136 of the sheath 126 is moved rearwardly through the aperture 58 in the front section 30 with one of the aligning notches 140, in the mounting end 136, receiving the aligning or positioning pin 122 therein. In this manner, the rotational position of the sheath 126 is fixed. Inward movement of the mounting end terminates with the positioning collar 138 seated against the end wall of the front section 30. The retaining cap 114, either previously positioned on the sheath 126 or at this point introduced over the arcuate forward end portion 142 thereof, is moved rearwardly and threaded onto the front section 30 with the forward wall or end 118 of the cap engaging the sheath collar 138 and clamping the collar 138, and hence the sheath itself, into fixed position on the forward end of the handle assembly 22. It is to be appreciated that the aperture 120 through the front wall of the cap 114 is such as to allow for free movement over the length of the sheath, while at the same time being sufficiently restrictive to positively engage against and confine the sheath collar 138.

When fully assembled, the blade 124 can be readily manipulated by either the thumb or index finger of a user while the instrument is held in one hand. A retraction of the internal slider 64, through a rearward sliding of the slide button 98, retracts the blade into a protected position completely within the sheath 126. Similarly, a forward movement of the slide button 98 effects a corresponding forward movement of the internal slider 64 and an extension of the blade to project beyond the leading end of the sheath and along a path determined by the curvature of the leading portion of the sheath. Thus, the sheath not only protects the blade but also guides and directs the blade whereby the extension of the blade from the sheath can actually comprise a cutting movement of the guided blade rather than merely a means for exposing the blade for subsequent manipulation. Basically, through the guide function of the sheath, the user, upon selection of the appropriated sheathed blade assembly with the curvature desired, properly orients the mounted sheath and then extends the blade with the blade cutting or slicing the tissue along the path of outward movement of the blade. In conjunction with the above, it is also to be appreciated that the blade itself is completely exposed, allowing for complete access thereto for use of the tip and/or edge as required and without interference from the guide structure provided by the sheath inward thereof.

As previously mentioned, the instrument is particularly adapted for use as a multi-functional probe, knife and aspirator/irrigator. When used to accommodate fluid flow, it is to be appreciated that the cap retained engagement of the collar 138 of the sheath 126 provides a fluid seal with the sheath 126 providing an internal flow path which combines and directly communicates with the aligned flow paths through the handle assembly itself.

I claim:

1. In a surgical instrument, a sheathed blade assembly, said assembly comprising an elongate sheath and an elongate surgical blade longitudinally received within said sheath for reciprocal movement therein, said sheath having forward and rear end portions, said sheath, other than for said forward end portion, being linear, said forward end portion being laterally directed away from the longitudinal axis of the remainder of said sheath and having a predetermined configuration defining a predetermined guide path away from said longitudinal axis, said forward end portion terminating in an open blade passing end, said blade having a forward surgical tip portion selectively projectable through and beyond said blade passing end and along the predetermined path defined by the forward end portion of the sheath through which the blade passes, said blade tip portion being completely retractable into said sheath, and means external of said sheath engaging said blade for a selective reciprocation thereof relative to said sheath and a selective extension and retraction of the tip end portion of the blade relative to the open blade passing end, said blade tip portion, when extended beyond said open blade passing end, being completely exposed.

2. The surgical instrument of claim 1 wherein said sheath, other than for said forward end portion, is of a cylindrical tubular configuration, said forward end portion having a flattened tubular configuration generally defining an oblong cross section.

3. The surgical instrument of claim 2 wherein said means external of said sheath engaging said blade for selective reciprocation thereof comprises an elongate handle mounting said sheath, said handle including an actuating mechanism engaging said blade, said actuating mechanism being finger manipulated for movement of said blade relative to said sheath.

4. A surgical instrument comprising, an elongate handle having a forward end portion, an elongate sheath having a proximal end portion, said handle including mounting means receiving and releasably mounting the proximal end portion of said sheath, said sheath extending longitudinally outward of the forward end portion of said handle, said sheath defining a full length hollow core, said sheath having a distal end portion, said distal end portion being laterally directed from the longitudinal axis of the remainder of the sheath and terminating in an open blade passing end, said laterally directed distal end portion defining a predetermined guide path away from said longitudinal axis within and beyond said sheath, an elongate flexible surgical blade longitudinally slidable within said sheath, said blade having a proximal end portion received within the forward end portion of said handle, said blade having a distal end portion received within the distal laterally directed end portion of the sheath for selective extension therefrom along the predetermined path defined by the laterally directed end portion of the sheath, said handle including blade positioning means engaged with the proximal end portion of the blade for effecting a selective extension and retraction of said blade for movement of said blade between a position wherein said blade distal end portion is completely received and enclosed within said sheath, and a position wherein said blade distal end portion is extended and completely exposed beyond the open blade passing end.

5. The instrument of claim 4 wherein said blade positioning means comprises a slide member having a forward end releasably engaging the proximal end portion of said blade, and an externally accessible finger manipulable element engaged with said slide member for movement thereof.

6. The instrument of claim 5 wherein said elongate handle includes a tubular body, said slide member being longitudinally positioned within said body, the forward end of said slide member defining a blade end retainer, the proximal end portion of said blade being configured to releasably lock within said retainer.

7. The instrument of claim 6 wherein said blade end retainer comprises a blade receiving opening with a laterally turned inner end, the proximal end portion of said blade including a laterally turned end, said blade proximal end portion being received and retained within said blade receiving opening with the laterally turned end of the blade fixed within the laterally turned inner end of the blade receiving opening.

8. The instrument of claim 7 including a forward section on said tubular body terminating in a forward end wall, said mounting means for mounting the proximal end portion of said sheath including an aperture defined through said forward end wall, and a retaining cap encircling the proximal end portion of said sheath and removably mounted on the forward section of said body with the proximal end portion of the sheath engaged between the cap and the forward end wall.

9. The instrument of claim 8 wherein said mounting means for mounting the proximal end portion of said sheath includes alignment means in said aperture, the proximal end portion of said sheath including an outwardly extending positioning projection thereon engageable against said forward end wall, said proximal end portion of said sheath further including a mounting end rearward of said positioning projection and longitudinally engageable within said aperture, said mounting end being configured to conform to said alignment means to preclude rotational movement of said mounting end within said aperture, said retaining cap being engageable against said positioning projection for a clamping thereof against said forward end wall.

10. The instrument of claim 9 wherein said alignment means comprises a pin radially directed inward of said aperture, said mounting end of said sheath including a longitudinal slot receiving said pin.

11. The instrument of claim 10 wherein said finger manipulable element includes a slide button slidably positioned on said body for longitudinal reciprocal movement, a connector fixing said button to said slide member for longitudinal movement of said slide member in response to movement of said button, and a longitudinally elongate slot through said body receiving said connector therethrough for accommodation of the longitudinal sliding movement.

12. The instrument of claim 11 wherein said longitudinally elongate slot has a laterally turned forward end for locking reception of said connector upon rotation of said button and slide member therewith for releasable locking of said slide member and button in a forward extended position, said forward extended position corresponding to the forward blade tip exposing position of said blade.

13. The instrument of claim 12 including torsion spring means engaged between said body and said slide member biasing said slide member rotationally in a direction engaging said connector within the laterally turned forward end of the longitudinally elongate slot in the body.

14. The instrument of claim 13 wherein said sheath, rearward of said distal end portion, is of a generally cylindrical configuration, the distal end portion of said sheath having a flattened reduced area cross-section.

15. The instrument of claim 14 wherein said elongate handle defines a fluid passage longitudinally therethrough, the hollow core of said sheath communicating with and comprising a continuation of said fluid passage, and means for effecting and controlling fluid flow through the fluid passage and sheath defined continuation thereof.

16. The instrument of claim 5 wherein said elongate handle defines a fluid passage longitudinally therethrough, the hollow core of said sheath communicating with and comprising a continuation of said fluid passage, and means for effecting and controlling fluid flow through the fluid passage and sheath defined continuation thereof.

17. The instrument of claim 7 wherein said handle includes an access opening selectively alignable with the blade receiving opening in the slide member for introduction of the proximal end portion of the blade into the blade receiving opening of the slide member.

18. The instrument of claim 4 wherein said sheath, rearward of said distal end portion, is of a generally cylindrical configuration, the distal end portion of said sheath having a flattened reduced area cross-section.

19. A disposable elongate sheath and blade module for use with a reusable handle module, said sheath and blade module comprising an elongate tubular sheath having a forward leading end portion laterally directed away from the longitudinal axis of the remainder of the sheath and terminating in an open forward end, and an elongate flexible blade longitudinally reciprocal within said sheath, said blade including a forward surgical tip portion selectively movable between a first position completely retracted within the laterally directed forward end portion of said sheath and a second extended position wherein said forward surgical tip portion of said blade is extended through and projected beyond the forward open end of said forward end portion for a complete exposure of said blade tip portion, said laterally directed end portion of said sheath defining a guide for said blade tip portion controlling the position and direction of said blade away from said longitudinal axis of said sheath as said blade is projected from said forward open end and therebeyond.

20. The disposable sheath and blade module of claim 19 wherein the laterally directed forward end portion of said sheath can vary and is predetermined in accord with contemplated procedural use of the blade.

21. The sheath and blade module of claim 19 wherein said laterally directed forward end portion defines an arcuate path for said blade.

22. The sheath and blade module of claim 21 wherein said sheath includes a rear end portion incorporating an outwardly extending positioning projection and a mounting end rearward of said positioning projection, said mounting end including an alignment slot therein.

* * * * *